United States Patent
Munce

(10) Patent No.: US 10,039,622 B2
(45) Date of Patent: Aug. 7, 2018

(54) METHOD FOR THE GUIDED REMOVAL OF DENTAL POSTS

(71) Applicant: C. John Munce, Santa Barbara, CA (US)

(72) Inventor: C. John Munce, Santa Barbara, CA (US)

(*) Notice: Subject to any disclaimer, the term of this patent is extended or adjusted under 35 U.S.C. 154(b) by 0 days.

(21) Appl. No.: 15/847,783

(22) Filed: Dec. 19, 2017

(65) Prior Publication Data
US 2018/0110595 A1    Apr. 26, 2018

Related U.S. Application Data

(60) Division of application No. 14/692,643, filed on Apr. 21, 2015, now Pat. No. 9,848,963, which is a continuation-in-part of application No. 13/748,102, filed on Jan. 23, 2013.

(60) Provisional application No. 61/589,733, filed on Jan. 23, 2012.

(51) Int. Cl.
*A61C 5/00* (2017.01)
*A61C 8/00* (2006.01)
*A61C 13/30* (2006.01)

(52) U.S. Cl.
CPC ............ *A61C 8/0089* (2013.01); *A61C 13/30* (2013.01)

(58) Field of Classification Search
CPC .............................. A61C 8/0089; A61C 13/30
USPC .................... 433/81, 224, 215, 221, 141–163
See application file for complete search history.

(56) References Cited

U.S. PATENT DOCUMENTS

| | | | |
|---|---|---|---|
| 3,330,040 A * | 7/1967 | Kahn | A61C 5/42 433/102 |
| 4,531,934 A | 7/1985 | Kossovsky et al. | |
| 4,746,292 A * | 5/1988 | Johnson | A61C 5/46 294/212 |
| 5,118,297 A | 6/1992 | Johnson | |
| 5,658,149 A | 8/1997 | Munce | |
| 5,839,896 A | 11/1998 | Hickok et al. | |
| 5,921,918 A * | 7/1999 | Riza | A61B 17/0218 600/204 |
| 6,227,855 B1 * | 5/2001 | Hickok | A61C 5/46 433/141 |
| 7,018,389 B2 | 3/2006 | Camerlengo | |
| 7,367,804 B2 * | 5/2008 | Lewis | A61C 5/46 433/127 |
| 2006/0234190 A1 | 10/2006 | Koch et al. | |
| 2009/0176189 A1 * | 7/2009 | Hof | A61C 5/46 433/141 |

* cited by examiner

*Primary Examiner* — Yogesh Patel
(74) *Attorney, Agent, or Firm* — Karish & Bjorgum, PC

(57) ABSTRACT

A method for removing a dental post from a tooth. The method includes (a) removing securing materials from around the dental post, (b) texturing the dental post to form a prepared dental post, (c) providing a dental post removal device with a hollow tubular structure and a fulcrum, (d) filling the hollow tubular structure with dental cement, (e) placing the dental cement-filled tubular structure over the prepared dental post, inserting a fluted file through the filled tubular structure and engaging file flutes between the prepared dental post and the wall of the tubular device and allowing the material to adhere together the tubular structure, the file, and dental post, and (f) applying a force on the fulcrum to remove the hollow tubular structure, the attached file and dental post from the tooth.

5 Claims, 13 Drawing Sheets

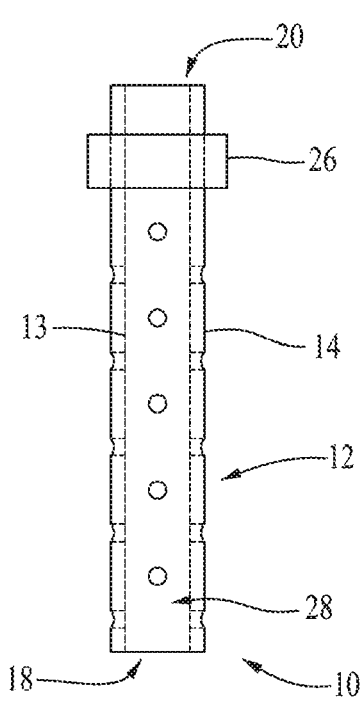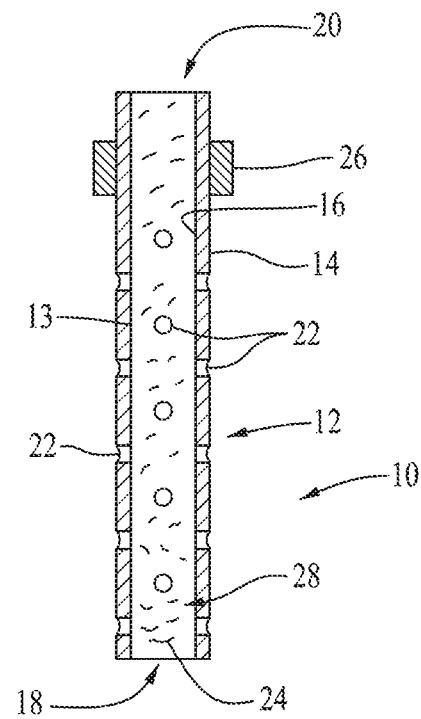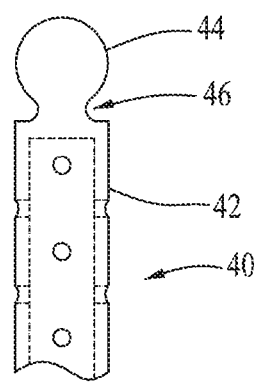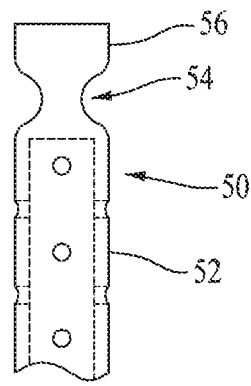

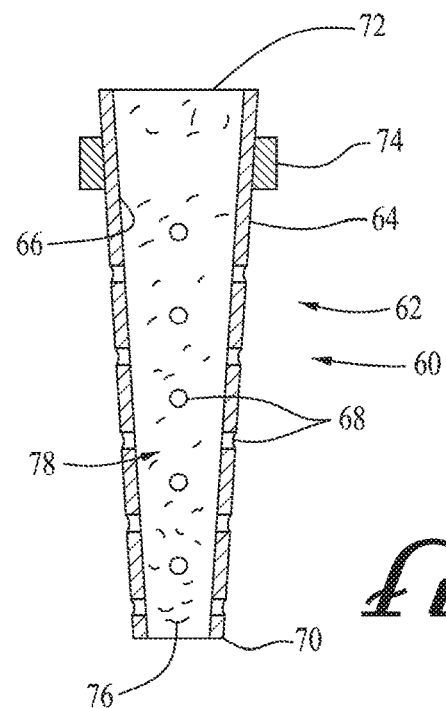
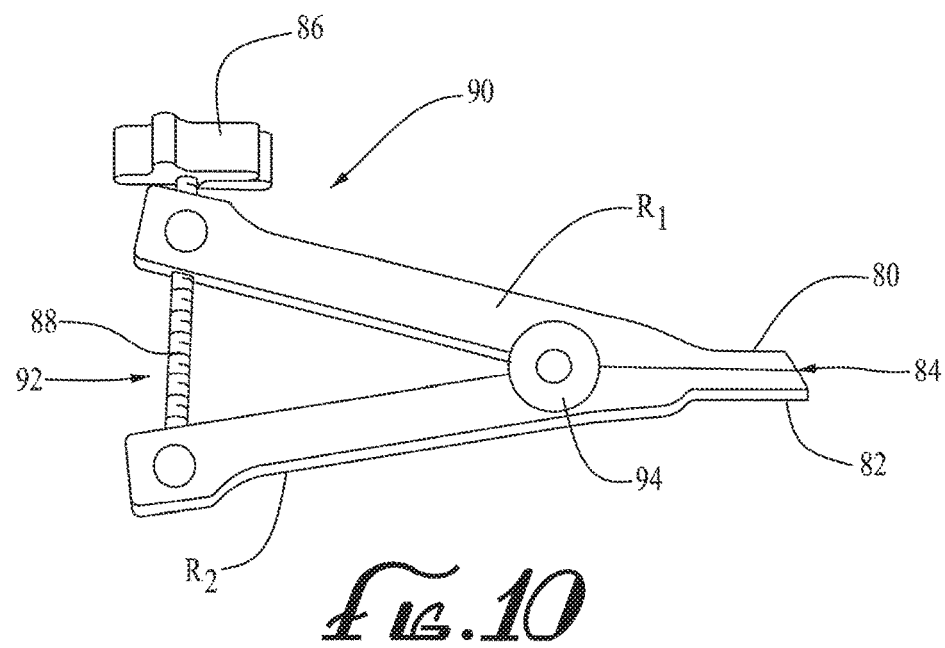

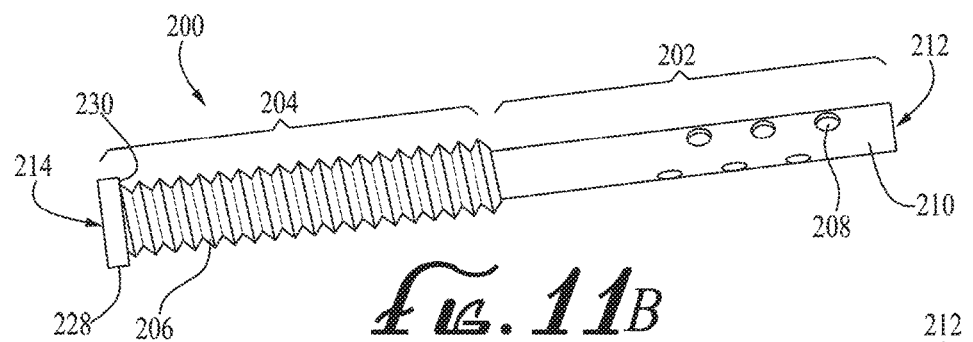
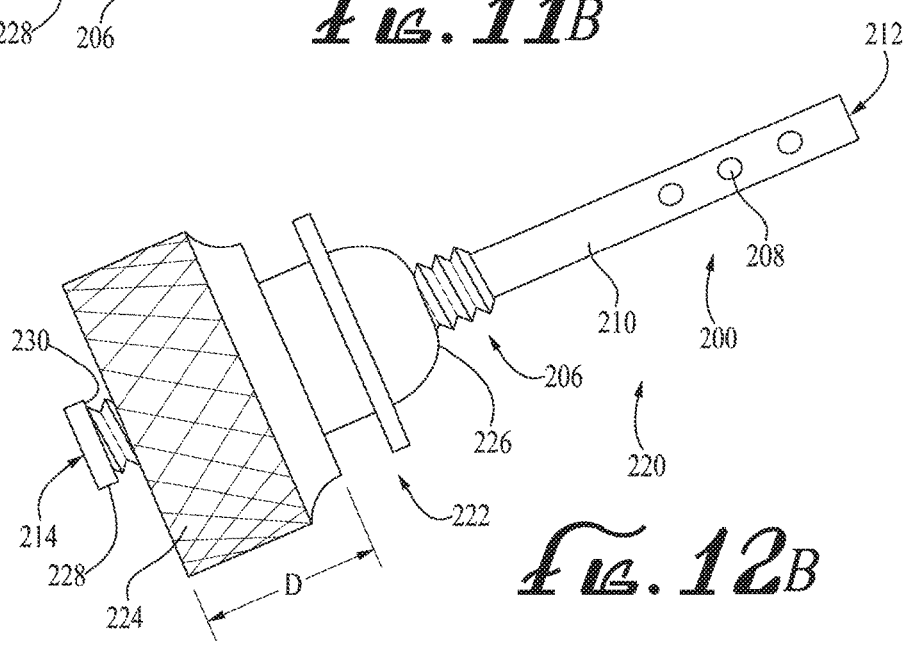

METHOD FOR THE GUIDED REMOVAL OF DENTAL POSTS

CROSS-REFERENCE TO RELATED APPLICATIONS

This application is a divisional patent application of U.S. patent application Ser. No. 14/692,643, filed Apr. 21, 2015, which is a continuation-in-part patent application of U.S. patent application Ser. No. 13/748,102, filed Jan. 23, 2013, entitled "Device and Method for Removing Dental Posts", which in turn claims priority from U.S. Provisional Patent Application No. 61/589,733, filed on Jan. 23, 2012, entitled "Device and Method for Removing Dental Posts."

SUMMARY

The invention relates to the field of instruments and methods for dentistry, and more particularly to a device and method for the guided removal of dental posts used with dental crowns. In cases where the amount of the tooth's natural crown portion (the part of the tooth that lies above the gum line) is insufficient, it may be necessary to build this area up. Reasons for lost crown include loss due to decay, fracture or being removed during root canal treatment. Dental posts may be metal posts that are cemented inside openings drilled into the tooth and are often used as part of the build up process. The dental post provides a way for the dentist to securely anchor the filling material core to the tooth. After the build up is concluded, a dental crown is placed to finalize the restoration and to completely seal off the root canal space.

While dental posts are useful in establishing dental restoration, it may become necessary to later remove the dental post, for example when the dental crown needs replacement or additional procedures need to be performed on the tooth, such as carrying out further endodontic treatment. Since the dental post is often tightly cemented or bonded into a tooth, and may not extend significantly above the gum line, it can be difficult for a practitioner to use forceps or other dental instruments to grasp the post and remove it. Indeed, doing so may place undue stresses and strains on tooth structure into which the post is imbedded and can possibly further damage the tooth. Furthermore, forceps alone may not apply to the post the degree of force or the vector of force required to safely dislodge many posts.

There accordingly remains a need for an improved device and method for the guided removal of a metal dental post. The invention provides a guided dental post removal device and method. The device comprises a tubular structure with a bore with side walls with an internal diameter and an external diameter. For the sake of this description, the tubular structure is described as having an upper open end and a lower open end, where the upper open end describes the end which extends out of the tooth and the lower end describes the end which is inserted into the tooth. Since the tubular device can be used on a maxillary or upper tooth or on a mandibular or lower tooth the terms "upper" and "lower" should not be read to imply "up" and "down" orientations. A series of openings can be formed through the sidewalls of the tubular structure. The series of openings are preferably formed at different levels along the long axis of the tubular structure and at various angular positions around the perimeter of the tubular structure, and will act to allow an infill material such as an auto-polymerizing composite resin, a cement, or other infill material to be filled into the tubular structure to mechanically connect to the tubular structure so that this infill material and the dental post received therein will not twist or pull out of the tubular structure. In addition to or in lieu of the series of openings, the inside of the sidewalls can have inward or outward projections, can be scored, textured, indented and/or coated with a high adhesion material that will strongly adhere to the composite resin, cement or other material that will infill the tubular structure's bore. Likewise, internal threads can be formed on the inside of the sidewalls, which internal threads will assist in bonding with an auto-polymerizing composite resin, a cement, or other infill material injected in the interior of the tubular structure and will also help engage with a file such as Hedstrom file inserted therein. A Hedstrom file is a coarse dental root canal files. Any other fluted file or an elongate tapered capture device will also function. As will be described further below, left handed threads may at times be beneficial because conventional Hedstrom files used with the tubular structure of the invention are right handed spiraled, and as such, when a Hedstrom file is screwed into the interior of the tubular structure, it will cross-thread with the left handed threads formed on the inside of the walls of the tubular structure and thereby tend to engage better with the tubular structure and the dental post to be removed, thereby providing improved removal results. However, the internal threads can be right hand threaded in which case they will normally engage with a right hand threaded Hedstrom file or can be left hand threaded and be adapted to engage with a specially designed left hand threaded Hedstrom file.

The tubular structure can include a collar or other fixing structure that extends along the tubular structure and will be positioned for access by a pulling tool. The fixing structure is preferably at or near the upper end of the tubular structure. The fixture structure can be in the nature of a collar that extends outwardly from the sidewalls of the tubular structure, can comprise a bulbous head that extends above the upper end of the tubular structure, can be an indent or groove formed in the sidewall, can be an internally-threaded nut that screws onto threads on the outside of the tube, a screw that screws into an upper end tubular structure, or some other structure or mechanism that is adapted to allow the fixing structure to be securely captured by a pulling tool. The fixture structure can be integrally formed with the tubular structure, (e.g., by welding, adhesive, or mechanical attachment, such as being crimped on), or the tubular structure and fixing structure can be formed of a single piece of material, such as by being machined or cast, or it can be attached via threads. In embodiment, instead of a stationary fixing structure, such as a collar, the device can include a movable fulcrum having a female threaded through hole formed therethrough, which movable fulcrum is designed to threadably engage with external male threads formed on the outside wall of the upper portion of tubular structure with the movable fulcrum being adapted to be threaded towards the unthreaded lower portion of the tubular structure during use, as will be described below.

Metallic dental posts come in various lengths and outer diameters, and to accommodate the various dental posts, a series of different sized dental post removal devices with varying lengths and internal diameters of the tubular structure will be provided.

The dental post will have been previously prepared as follows. First, any build up material that was formed around the dental post will be removed, such as by a dental drill or ultrasonic tip. For example, a #½ or #¼ deep dental bur will be used to dissect cement from around the dental post. Once the dental post is free from build up material, then a series of generally horizontal notches or grooves will be formed along different levels and angular positions of the outer sidewall of the dental post. This can be accomplished with a wheel bur, such as offered by Brasseler USA, or other dental instruments. To avoid unduly weakening the integrity of the dental post, such that it might snap off when being removed, the notches should not extend too deeply into the walls of the dental post, and should not completely circumnavigate the dental post. After the dental post is prepared, it should be cleaned and dried. If desired, it may also be coated with an accelerator or other type of surface preparation chemical which can enhance the adhesion of the material such as an auto-polymerizing composite resin, cement, or other material to the post.

The practitioner will then select the most ideally sized dental post removal device to accommodate the dental post. It may be preferable that the wall structure of the dental post removal device be formed of a deadsoft material so that it can be adjusted (e.g., bent) to easily fit onto the dental post. Before proceeding, the practitioner should trial fit the dental post removal device onto the dental post in order to ensure that it fits well and to ensure that the dental post removal device can be quickly engaged with the dental post once the dental post removal device is charged with composite, cement or other material. An aggressively-fluted endodontic file (such as a Hedstrom file) of appropriate length and diameter (or another elongate and preferably tapered capture device) is then selected, inserted through the open end of the tube, and test-threaded clockwise into the tube, tightly securing itself against the lumen of the tube while becoming engaged into notches on the prepared post. This file is then removed and set aside for later re-insertion. Likewise, the tube of the dental post removal device is also removed in order to prepare it for the next step.

A high strength and fast curing composite resin, cement or other infill material will be injected (e.g., with a syringe) into the lower opened end of the tubular structure and fill it until the infill material exits the opposite opened end of the tubular structure. An example of an excellent infill material for this purpose includes RapidCore® from Centrix®; however, other high strength composite resins or cements for metal to metal adhesion or other materials can be used. If composite is used, it must be an auto-polymerizing type of composite because light-initiated polymerization is ineffective when the material is within the tubular structure of the device. The RapidCore® composite resin will begin to set up immediately and cures in as little as two minutes. Once the composite resin, cement or other infill material is introduced into the interior of the tubular structure, a finger or thumb is placed over the open end of the tube to prevent the material from being forced out the open end of the tube, the tube is quickly fitted over the dental post which has been prepared, and the prior-fitted aggressively-fluted file is immediately re-inserted into the open end of the tube and clockwise rotated to mechanically secure it within the tube alongside the prepared post. The infill material is allowed to set or polymerize undisturbed. On insertion of the tube onto the post, any infill material that is forced out through any openings formed in the sidewalls of the tubular structure will not adversely affect the operation of the device. The infill material will fill in the space in the interior of the tubular structure around the dental post with its grooves or notches formed thereon and adhere to any inward or outward projections, interior scoring, texturing, threads, and/or coating of the sidewalls and lock into the series of any openings formed through the sidewalls of the tubular structure. Thus, the material will effectively lock the dental post together with the tubular structure of the dental post removal device. This will allow a dental post that is tightly cemented or bonded to a tooth to be safely removed.

After adhesion of the device of the invention to the mechanically-secured file and post, an expansion plier, such as a modified version of a Ruddle Post Remover tool, the Gonon Post Remover tool, the Thomas Post Remover tool, the Easy X-TRACTOR (A-Titan Instruments), the UPR (Universal Post Remover-Dent Corp), the Outpost (San Diego Swiss Machining) or another similar device, is used to gradually pull outwardly on the dental post removal device and its attached file and dental post. The expansion pliers can be designed to include at its moving end, a catch for engaging the stationary fixing structure or movable fulcrum of the dental post removal device. To be more effective for removal of threaded posts, this pulling device may also be developed in such a way as to apply selectively a rotational force during the extraction process which rotational force may be either clockwise or counter-clockwise and may also be de-selected. Regarding the matter of a rotational force selectively applied during the extraction process, if such rotational force were to be counter-clockwise in order to "unscrew" a clockwise-threaded post, then the Hedstrom file should be left-hand fluted so as not to unscrew itself during the counter-rotation of the apparatus during operation. A stationary end of the expansion pliers will be supported on the tooth from which the dental post is being removed. A rubber "insulator" is typically included with the Ruddle device and other similar devices. The insulator provides an interface between the "stationary end" of the Ruddle pliers and the tooth structure on which it will rest when applied.

Another methodology that the inventor uses to off-lay some of the potentially damaging force that can be generated on the cusp tips of compromised tooth structure is as follows. The inventor places a hollow plastic cone over the exposed post with the larger diameter of the cone extending outward from the tooth, and then injects a non-bonded auto-polymerizing composite or similar material in the space around the outside of conical tube to fill the cavity space up to the occlusal surface of the tooth and beyond, covering all delicate coronal structure. On polymerization (or setting if not a composite), the plastic cone is removed, and the surface of the material is flattened. This flattened surface provides a robust platform against which to rest that portion of the expansion pliers. The advantage of this over the insulator is that it distributes the considerable force of the pliers throughout the entire coronal structure of the tooth, and not just against the high points of the cusp tips or the perimeter of the cavity preparation as does the rubber insulator. Since the material is not bonded into the tooth, but is only injected passively into the cavity and over the coronal perimeter, after the post is removed, the material is easily removed with dental burs or sometimes with only a simple slight nudge from a hand instrument. The expansion pliers are accordingly used to apply a pulling force to the dental post and remove it from the tooth. The expansion pliers generates considerable mechanical advantage and includes a screw knurl, which when turned, provides the pulling force. Other pulling types of tools can be used with the pulling force being preferably generated along the same axis as the dental post being removed.

As noted above, the dental post removal device can be provided as a series of different tubular structures with parallel or generally parallel side walls having inner and outer diameters to accommodate different sized dental posts.

In lieu of providing such a series of different sized tubes of uniform inner and outer diameter, the invention also contemplates providing a dental post removal device with a generally conical-shaped tubular structure with a narrower open end that widens as it progresses upwardly towards either an opened or a closed end. In such an embodiment, the walls can be of uniform thickness so that the lumen passing therethrough will be conical and the outer shape will also be generally conical. Alternately, the outer diameter can remain constant while only the inner lumen is conical, in which case the wall thickness will vary. When the wider end is open, it accommodates the insertion of a Hedstrom file. The standard Hedstrom file has a 02 taper, so providing a slight internal flare of this version of the post removal device—for example a 04 taper-would facilitate a tight adaptation of the 02-tapered file to the flare/taper of the inner wall of the device. With this embodiment, if the dental post is of a larger diameter than the open end of the generally conical-shaped tubular structure, the practitioner can cut off a section of the tubular structure so that the open end is large enough to receive the dental post. The end can be cut off with a wheel saw or other commonly available dental instruments. One feature of this embodiment, besides not needing to provide a series of dental post removal devices with different sized tubular structures, is that as a pulling force is exerted on the dental post removal device, the mass of composite, cement or other material formed inside the conical shaped tubular structure around the dental post will be generally frustum conical in shape and will accordingly not be able to pull through the smaller opening.

As a result of using the dental post removal devices and method of the invention, dental posts that are stubbornly affixed in a tooth, even in difficult to access locations, can be reliably removed while minimizing potential stress to the remaining tooth structure to which the dental post is affixed and surrounding teeth and tissue.

BRIEF DESCRIPTION OF THE DRAWINGS

FIG. 1 is a front view of an exemplary embodiment of a dental post removal device of the invention.

FIG. 2 is a longitudinal cross-sectional view of the dental post removal device of FIG. 1.

FIG. 3 is a detail showing an exemplary embodiment of another dental post removal device of the invention.

FIG. 4 is a detail showing yet another exemplary embodiment of a dental post removal device of the invention.

FIG. 5 is a longitudinal cross-sectional view showing a further exemplary embodiment of a dental post removal device of the invention.

FIG. 10 is a side view of a Ruddle post pulling tool used with the dental post removal device of the invention.

FIG. 11B is a front view of yet another exemplary embodiment of a tubular structure of a dental post removal device of the invention.

FIG. 12B is a front view of the exemplary embodiment of the tubular structure of FIG. 11B engaged with a movable fulcrum.

DETAILED DESCRIPTION

Figure 6:
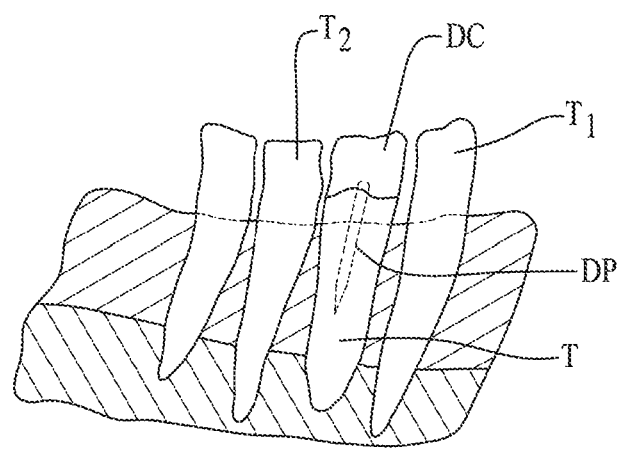
FIG. 6 is a diagrammatic view showing a tooth with a dental post and a dental crown before the dental post is exposed.

FIG. 1 is a front view of an exemplary embodiment of a dental post removal device 10 of the invention and FIG. 2 is a longitudinal cross-sectional view thereof. The dental post removal device 10 includes a tubular structure 12 with sidewalls 13 with an outer surface 14 and an inner surface 16. The tubular structure 12 has two open ends, 18 and 20 and has a bore 28 running therethrough. A series of through holes or openings 22 are preferably formed through the tubular structure 12. The tubular structure 12 will preferably have sidewalls 13 consisting of parallel side walls and will be formed of strong metal. The metal can be non-pliable, or pliable. In addition to metal, the tubular structure can be formed of other materials such as composite materials including para-aramid synthetic fiber. The series of openings 22 are preferably at different vertical levels along the long axis of the tube 12 and at different angular positions around the circumference. The series of openings 22 will act to allow composite resin, cement or other material to be filled into the bore 28 of the tubular structure 12 to mechanically connect to the tubular structure 12 so that, upon polymerizing, setting or curing, the composite resin, cement or other material and the dental post received therein (see FIGS. 9a and 9b) will not twist or pull out of the tubular structure 12. In addition to or in lieu of the series of openings 22, the inner surface 16 of the sidewalls 13 can be scored, textured, and/or coated with a high adhesion material 24 or other type of surface preparation chemical which can enhance the adhesion of a composite resin, cement or other material. Likewise, rather than including a series of openings formed in the tube or having the inside of the tube scored, textured, and/or coated with a high adhesion material or other type of surface preparation chemical which can enhance the adhesion, the tubular structure 12 can have dimples (not shown) and/or internal threads formed on the inner surface 16 of the sidewalls 13. These structural features are referred to herein as "engaging features." The tubular structure 12 further includes a collar or other fixing structure 26 that extends outwardly from the tubular structure and will be positioned for access by a pulling tool. The fixing structure 26 is preferably at or near end 20 of the tubular structure 12. The fixture structure 26 can be in the nature of a collar that extends outwardly from the sidewalls of the tubular structure.

Alternatively, as shown in FIG. 3, a dental post removal device 40 can include as a fixing structure a bulbous head 44 contiguous with a narrower neck 46 that is contiguous on its opposite side with a tubular structure 42; or, as shown in FIG. 4, a dental post removal device 50 can comprise an indent 54 formed in the tubular structure 52 contiguous with a wider end 56 on its opposite side. Other fixing structures that are adapted to allow the fixing structure to be securely captured by a pulling tool can also be used, such as indent(s) or groove(s) formed in the sidewall, an internally-threaded nut that screws onto threads on the outside of the tube, a screw that screws into an upper end tubular structure, or some other structure or mechanism that is adapted to allow the fixing structure to be securely captured by a pulling tool. The fixture structure can be integrally formed with the tubular structure, (e.g., by welding, adhesive, or mechanical attachment, such as being crimped on), or the tubular structure and fixing structure can be formed of a single piece of material, such as by being machined or cast, or it can be attached via threads. Whatever embodiment of fixture structure used, it can be integrally formed with the tubular structure, (e.g., by welding, adhesive, mechanical attachment such as being crimped on), detachably screwed on, or the tubular structure and fixing structure can be formed of a single piece of material. The tubular structure can, if desired, be formed of deadsoft material that can be formed (e.g. bent) to accommodate the needs of the practitioner. A series of the dental post removal devices 10, 40, 50 can be provided having different gauge tubular structures to best fit different sized dental post to be removed.

FIG. 5 is a longitudinal cross-sectional view showing a further exemplary embodiment of a dental post removal device 60. In lieu of providing a series of different sized tubular structures, the invention also contemplates providing a dental post removal device 60 with a generally conically-shaped tubular structure 62 with a narrower open end 70 that widens as it progresses in its long axis towards the opposite end 72. The conically-shaped tubular structure 62 has an outer surface 64 and an inner surface 66. A series of openings 68 may be formed through the conically-shaped tubular structure 62. A collar or other fixing structure 74 that extends outwardly from the tubular structure 62 will be provided for engagement with a pulling tool. The fixing structure 74 is preferably located at or near the wider end 72 of the device 60. Although the tubular structure 62 is shown as having a significant taper, it need only be slightly tapered. The fixture structure 74 can be in the nature of a collar that extends outwardly from the sidewalls of the tubular structure. Alternatively, it can be a bulbous head or an indent formed on the body of the device (similar to FIGS. 3 and 4.) With this particular embodiment of the dental post removal device 60, if the diameter of the dental post is larger than the open end 70 of the conically-shaped tubular structure 62, the practitioner can cut off a section of the smaller-diameter end of the conical structure 62 so that the newly created open end 70 is large enough to receive the dental post. The end can be cut off with a wheel saw or other commonly available dental instruments. Besides not needing to provide a series of dental post removal devices with different sized tubular structures, this embodiment has an additional benefit. Since the mass of cement formed inside the conically-shaped tubular structure around the dental post will be generally frustum conical in shape, it will not be able to pull through the smaller opening as a pulling force is exerted on the dental post removal device.

FIG. 6 is a diagrammatic view showing a tooth T with a dental post DP and a dental crown DC before the dental post DP is exposed. As shown, the tooth T is located between two other teeth $T_1$ and $T_2$.

Figure 7:
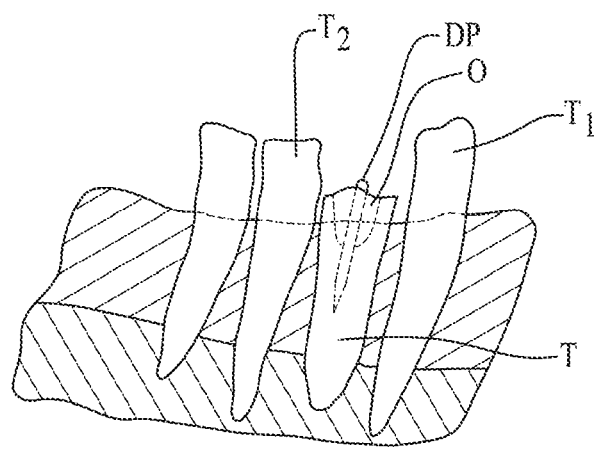
FIG. 7 is a diagrammatic view showing a tooth with a dental crown removed and with tooth structure partially removed around the dental post to partially expose the dental post.

FIG. 7 is a diagrammatic view showing a tooth T with a dental crown DC removed and with the tooth structure partially removed to form a cavity O around the dental post P to partially expose the dental post DP. Tooth T is shown between teeth $T_1$ and $T_2$.

Figure 8:
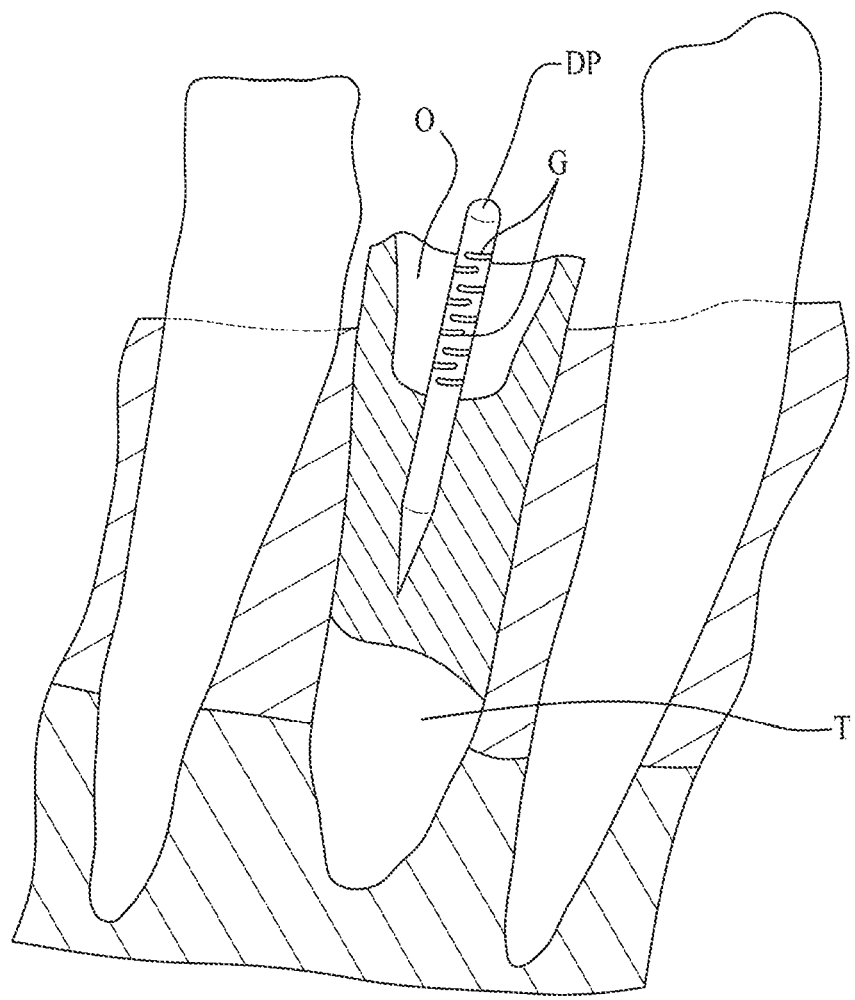
FIG. 8 is a diagrammatic view showing the dental post after it is notched.

FIG. 8 is a diagrammatic view showing the dental post DP after being prepared by having a series of grooves or notches cut into its sidewalls. The dental post DP will have been previously prepared as follows. First, any build up material that was formed around the dental post DP will be removed, such as by a dental drill or ultrasonic tip, and a cavity O may be formed in the tooth T around the dental post DP if necessary in order to expose the post adequately. For example, a #½ or #¼ Munce Discovery Bur Deep Trougher will be used to dissect cement from around the dental post DP. Once the dental post DP is free from build up material, cement and encroaching tooth structure, then a series of generally horizontal notches or grooves G will be formed along different levels and angular positions around the outer sidewall of the dental post DP. This can be accomplished with a wheel bur, such as offered by Brasseler USA, or other dental instruments. To avoid unduly weakening the integrity of the dental post DP, such that it might snap off when being removed, in cases where the post is of a relatively small diameter, the notches or grooves G should not extend too deeply into the walls of the dental post DP, and preferably nor should the notches be formed all the way around to form a collar groove on the dental post DP. After the dental post DP is prepared, it should be cleaned and dried. If desired, it may also be coated with an accelerator which can enhance the adhesion of the material such as an auto-polymerizing composite resin, cement, or other material to the post.

The practitioner will then select the most ideally sized dental post removal device to accommodate the dental post DP. It may be preferable that the wall structure of the dental post removal device be formed of a deadsoft material so that it can be adjusted (e.g., bent) to easily fit onto the dental post. Before proceeding, the practitioner should trial fit the dental post removal device onto the dental post in order to ensure that it fits well and to ensure that the dental post removal device can be quickly engaged with the dental post once the dental post removal device is charged with composite resin, cement or other material. While the device remains trial-fitted on the post, a Hedstrom file is trial-inserted through the open end to the point where it has engaged the notched post and thereafter been right-hand rotated with inward pressure so as to fully ensure that it will fully lodge itself between the post and the wall of the tube. Once the properly-sized Hedstrom file has been selected and trial-inserted as above, the file is removed and set aside as is the dental post removal device.

Next, in order to use the dental post removal device 10, 40, 50, 60 of the invention, a high strength and fast polymerizing composite resin, cement or other material C (see FIG. 9a) will steadily be injected (e.g., with a syringe) into one of the open ends 18 or 20 of the tubular structure 12, while withdrawing the injecting end of the syringe from the tube. This is done until the material C has completely filled the tube and has begun to exit the series of openings 22 formed through the sidewalls of the tubular structure 12 and also exits the opposite opened end of the tubular structure 12. Any excess material may be removed before it cures, sets or polymerizes. An acceptable material for this purpose includes RapidCore® composite from Centrix®; however, other high strength composite resins, cements or other materials for metal to metal adhesion can be used. The RapidCore® composite will begin to set up immediately and polymerizes in as little as two minutes. Once the material C is introduced into the interior of the tubular structure 12 and any excess material is removed, the tubular structure 12 is quickly fitted over the dental post DP which has been prepared. The selected Hedstrom file is then immediately inserted through the open end of the tube to the level where it begins to engage the prepared post and then right-hand rotated so as to be threaded into the tube fully engaging itself between the post and the wall of the tube. Speed is important here because of the polymerization or setting process of the material which will already be underway. The material inside the device is allowed to polymerize, set or cure undisturbed, affixing each element of the multi-part device into a single unit. Once set, cured or polymerized, any additional material C that has been pushed out of the channel formed in the tubular structure by the dental post DP through the openings 22 formed in the sidewalls of the tubular structure 12, can be removed, if desired, with an instrument, so that it does not extend into cavity O formed in the tooth T around the dental post DP. However, removing these excess "bullets" of material is not really required, but if it does take place, it should only be done after the material completely sets or polymerizes. The composite resin, cement or other material C will fill in the space in the interior of the tubular structure around the dental post DP with its grooves or notches G formed thereon as well as around the flutes on the engaged Hedstrom file and adhere to any interior scoring, texturing, and/or coating of the sidewalls, or other engaging features (e.g., internal dimples) of the tubular structure, and lock into the series of openings 22 formed through the sidewalls of the tubular structure. Thus, the material C will effectively permanently lock the dental post DP and the Hedstrom file together with the tubular structure 12 of the dental post removal device 10. This will allow a dental post DP that is tightly cemented or bonded in place in a tooth to be safely removed.

Figure 9A:
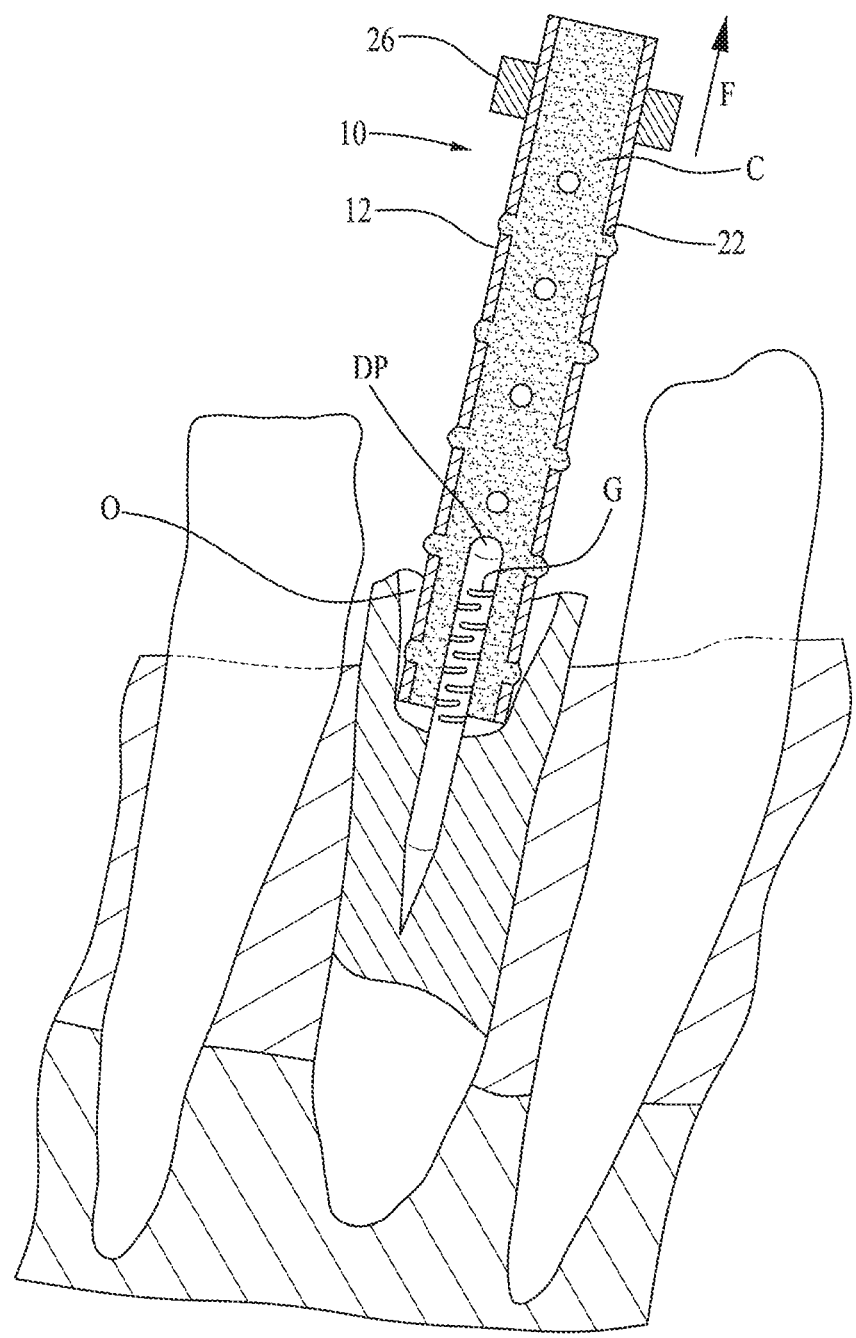
FIG. 9a is a diagrammatic view showing the notched dental post with a dental post removal device slid on over the dental post, and with composite resin, cement or other material filling the space in the dental post removal device around the dental post to secure the dental post removal device and the dental post together, just prior to being removed together from the tooth.

FIG. 9A is a diagrammatic view showing the notched dental post DP with a dental post removal device 10 slid on over the dental post DP and with dental composite resin, cement or other material C filling the space in the dental post remover tool around the dental post DP and extending into the openings 22 formed in the sidewalls of the dental post removal device 10 to secure the dental post remover tool and the dental post DP together, just prior to being removed together from the tooth.

Figure 9B:
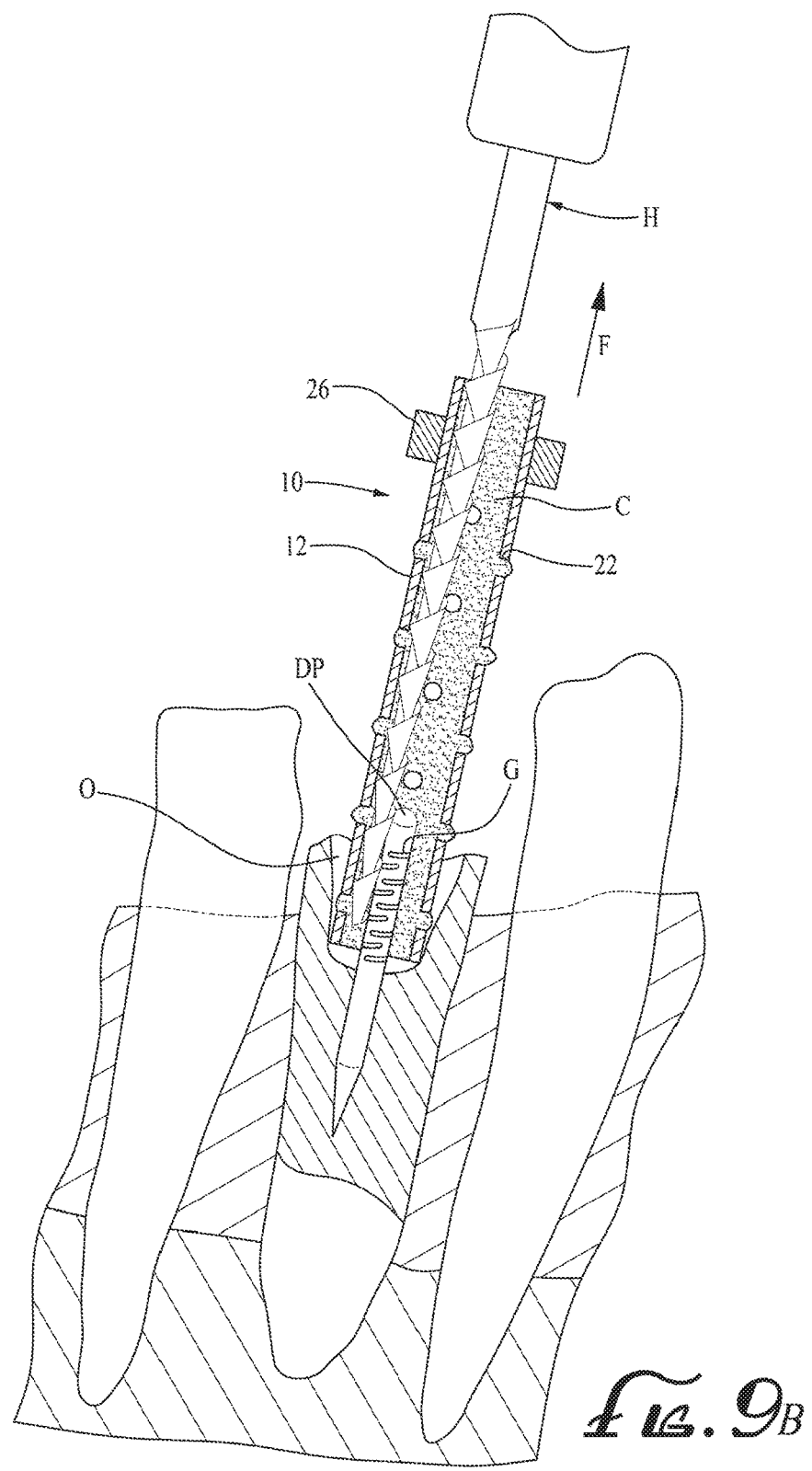
FIG. 9b is a diagrammatic view showing the tooth, post and device of FIG. 9a just prior to the setting of the composite with a Hedstrom file inserted through the open end to the point where it has engaged the notched post and thereafter been right-hand rotated with inward pressure so as to fully lodge itself between the post and the wall of the dental post removal device, thus adding significantly to the "adhesion" of the 4-element device (tube, composite, post, and now Hedstrom file).

FIG. 9B is a diagrammatic view showing the tooth, post and device of FIG. 9a just prior to the setting of the composite with a Hedstrom file H inserted through the open end to the point where it has engaged the notched post and thereafter been right-hand rotated with inward pressure so as to fully lodge itself between the post and the wall of the tube, thus adding significantly to the "adhesion" of the 4-element device (tube, composite, post, and now Hedstrom file).

FIG. 10 is a side view of a Ruddle post remover tool 90, a pulling device used with the dental post remover tool of the invention. The Ruddle post remover tool 90 has a dental post removal tool engaging lever portion $R_1$ and a tooth engaging lever portion $R_2$. The dental post removal tool engaging lever portion $R_1$ has a dental post removal tool engaging end 80 and the tooth engaging lever portion $R_2$ has a tooth contact end 82 at a distal end 84 of the device. A knurl 86 is positioned on a threaded shaft 88 near a proximal end 92 of the device which passes through the dental post removal tool engaging lever portion $R_1$ and the tooth engaging lever portion $R_2$. By rotating the knurl 86 in a clockwise direction this brings the two proximal ends closer and moves the two distal ends apart from each other. The dental post pulling tool engaging lever portion $R_1$ and the tooth engaging lever portion $R_2$ are pivoted together by a pivot 94 that is closer to the distal end 84 than the proximal end 92, and can accordingly generate considerable mechanical advantage. After adhesion is established, an extraction tool, such as a modified version of a Ruddle post pulling tool, is used to gradually pull outwardly on the dental post removal device and its attached dental post. The Ruddle post pulling tool can include at its moving end a catch for engaging the fixing structures 26, 44, 54, 74 of the dental post removal devices 10, 40, 50, 60, respectively. The distal end of the Ruddle post pulling tool's tooth engaging lever portion $R_2$ will be supported on the tooth T from which the dental post DP is being removed and the distal end of dental post removal tool engaging lever portion $R_1$ will be engaged with the fixing structure 26, 44, 54, 74 of the dental post removal device 10, 40, 50, 60, respectively. By rotating the knurl 86 in a clockwise direction, a force F will pivot the dental post pulling tool engaging end 80, causing it to pull its attached dental post DP out of the tooth T. In practice, once the adhesion between the dental post DP and the tooth T to which it is affixed is broken, the dental post DP can generally be easily withdrawn.

Turning to FIGS. 11-21, there are shown views of another embodiment of a threaded hollow tubular structure 100 for the guided removal of dental posts (as shown in FIG. 8.)

Figure 11A:
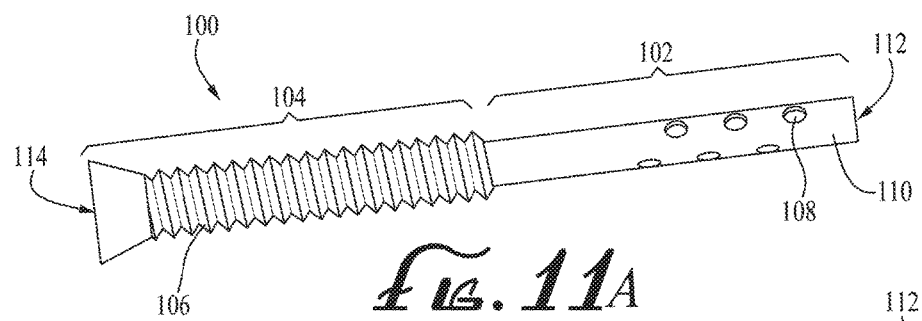
FIG. 11A is a front view of another exemplary embodiment of a tubular structure of a dental post removal device of the invention.
Figure 12A:
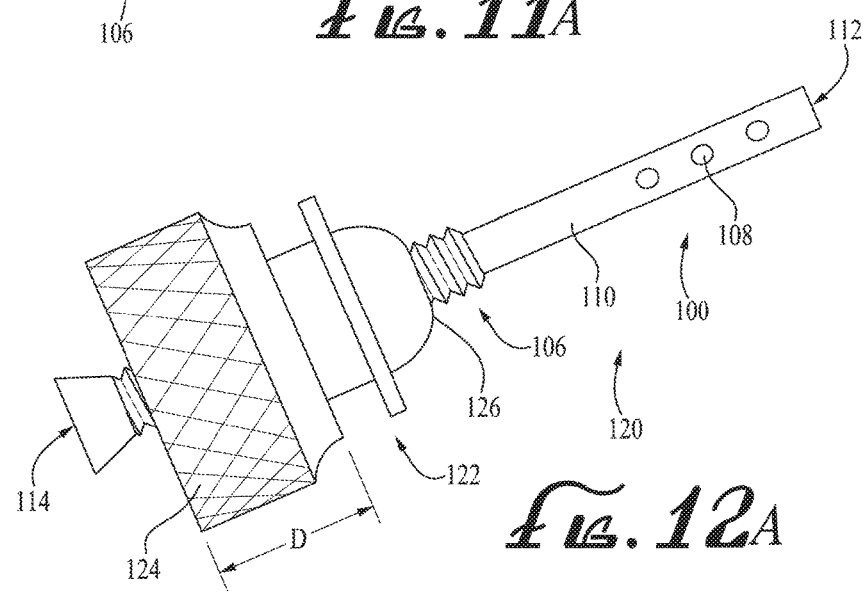
FIG. 12A is a front view of the exemplary embodiment of the tubular structure of FIG. 11A engaged with a movable fulcrum.

FIG. 11A is a front view the exemplary embodiment of the tubular structure 100 of a dental post removal device of the invention 120 which is shown with its movable fulcrum 122 attached to the tubular structure 100 in FIG. 12A. As shown, the hollow tubular structure 100 has a proximal region 102, and a distal externally threaded region 104 with male threads 106 formed thereon. The proximal region 102 is shown as having a series of optional peripheral holes 108 formed through the sidewall 110 thereof. These optional peripheral holes 108 will help to retain infill material to be injected into the hollow tubular structure 100 in the same manner as discussed with the dental post removal device 10 of FIGS. 1-9B above. However, in addition to or in lieu of the series of holes 108, the inside of the sidewalls 110 can have inward or outward projections, can be scored, textured, indented and/or coated with a high adhesion material or other type of surface preparation chemical which can enhance the adhesion of composite resin, cement or other material that will infill the tubular structure's bore, and best yet, can have internal threads formed thereon. Use of internal threads formed on the inside of the sidewalls will assist in bonding with cement injected in the interior of the tubular structure and engage with the Hedstrom file. Left handed threads can sometimes be useful because Hedstrom files used with the tubular structure of the invention are right hand spiraled, and as such, when a Hedstrom file is screwed into the interior of the tubular structure, it will cross-thread with the left handed threads formed on the inside of the walls of the tubular structure and thereby tend to engage better with the tubular structure and the dental post to be removed, thereby providing improved engagement of the tubular structure, the dental post, and the Hedstrom file, and better removal results. However, right hand internal threads and right hand threads on the Hedstrom file or left hand internal threads and a Hedstrom file with left handed threads could provide a better lock between the Hedstrom and inner threads. Left handed internal threads could be useful, however, in the case of a threaded post that is being removed because a threaded post will virtually always be right hand threaded, and so left hand threads inside the tube would definitely be preferred to allow left handed rotation of the tube without unscrewing the tube from the inner threads—in fact, rotating in the left hand direction would "tighten" the composite on the threads while at the same time putting an unscrewing rotation onto the target threaded post. The tubular structure 100 has a proximal end 112 and a distant end 114. The distal end 114 is shown as being mushroomed out so as to prevent the movable fulcrum 122 from being removed from the distal end 114. The length of the distal externally threaded region 104 with male threads 106 is preferably long enough to allow the movable fulcrum 122 to be moved a substantial distance D along the externally threaded region 104 by turning the movable fulcrum 122. The movable fulcrum 122 preferably has a grasping region, such as a knurled rim 124, and a front region 126 that will impinge on the dental post pulling tool engaging end 80 as described further below regarding FIGS. 18-20. The movable fulcrum 122 will be screwed onto the externally threaded region 104 by a user, e.g., a dentist, who grasps and turns the knurled rim 124 to bring the movable fulcrum 122 closer to the open end of the tubular structure 100 that captures the dental post.

FIG. 11B is a front view yet another exemplary embodiment of a tubular structure 200 of a dental post removal device of the invention 220 which is shown with its movable fulcrum 222 attached to the tubular structure 200 in FIG. 12B. As shown, the hollow tubular structure 200 has a proximal region 202, and a distal externally threaded region 204 with male threads 206 formed thereon. The proximal region 202 is shown as having a series of optional peripheral holes 208 formed through the sidewall 210 thereof. These optional peripheral holes 208 will help to retain infill material to be injected into the hollow tubular structure 200 in the same manner as discussed with the dental post removal device 10 of FIGS. 1-9B above. However, in addition to or in lieu of the series of holes 208, the inside of the sidewalls 210 can have inward or outward projections, can be scored, textured, indented and/or coated with a high adhesion material or other type of surface preparation chemical which can enhance the adhesion of composite resin, cement or other material that will infill the tubular structure's bore, and best yet, can have internal threads formed thereon. Use of internal threads formed on the inside of the sidewalls will assist in bonding with composite resin, cement or other material injected in the interior of the tubular structure and engage with the Hedstrom file. Left handed threads can sometimes be useful because Hedstrom files used with the tubular structure of the invention are right hand fluted, and as such, when a Hedstrom file is screwed into the interior of the tubular structure, it will cross-thread with the left handed threads formed on the inside of the walls of the tubular structure and thereby tend to engage better with the tubular structure and the dental post to be removed, thereby providing improved engagement of the tubular structure, the dental post, and the Hedstrom file, and better removal results. However, right hand internal threads and right hand threads on the Hedstrom file or left hand internal threads and a Hedstrom file with left handed threads could provide a better lock between the Hedstrom and inner threads. Left handed internal threads could be useful, however, in the case if a threaded post that is being removed because a threaded post will virtually always be right hand threaded, and so left hand threads inside the tube would definitely be preferred to allow left handed rotation of the tube without unscrewing the tube from the inner threads—in fact, rotating in the left hand direction would "tighten" the composite on the threads while at the same time putting an unscrewing rotation onto the target threaded post. The tubular structure 200 has a proximal end 212 and a distant end 214. Located at the distal end 214 is an enlarged ring 228 which has a frontward seat 230 which will prevent the movable fulcrum 122 from being screwed completely off the distal end 214 of the tubular structure 200. The enlarged ring 228 can be formed together with the tubular structure 200 or can be in the form of a nut that is permanently affixed to the end of the tubular structure 200. The length of the distal externally threaded region 204 with male threads 206 is preferably long enough to allow the movable fulcrum 222 to be moved a substantial distance D along the externally threaded region 204 by turning the movable fulcrum 222. The movable fulcrum 222 preferably has a grasping region, such as a knurled rim 224, and a front region 226 that will impinge on the dental post pulling tool engaging end 80 as described further below regarding FIGS. 18-20. The movable fulcrum 222 will be screwed onto the externally threaded region 204 with its front region 226 facing the proximal region 202 by a user, e.g., a dentist, who grasps and turns the knurled rim 224 to bring the movable fulcrum 222 closer to the open end 212 of the tubular structure 200 into which the dental post is captured.

Figure 13:
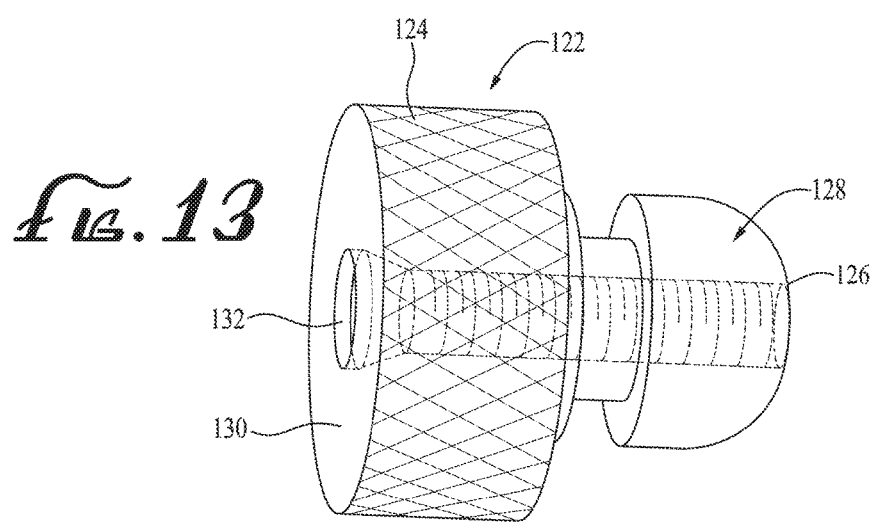
FIG. 13 is a detail isometric view showing the exemplary movable fulcrum.

FIG. 13 is a detail isometric view showing the movable fulcrum 122, its knurled rim 124 and its front region 126. The front region 126 can have a domed shape 128. A back end 130 is shown with a threaded through hole 132 formed axially through the moving fulcrum 122 and exits at its front region 126. As shown, the through hole 132 widens out at its very end and acts to prevent removal of the movable fulcrum 122 from the tubular structure 100.

Figure 14:
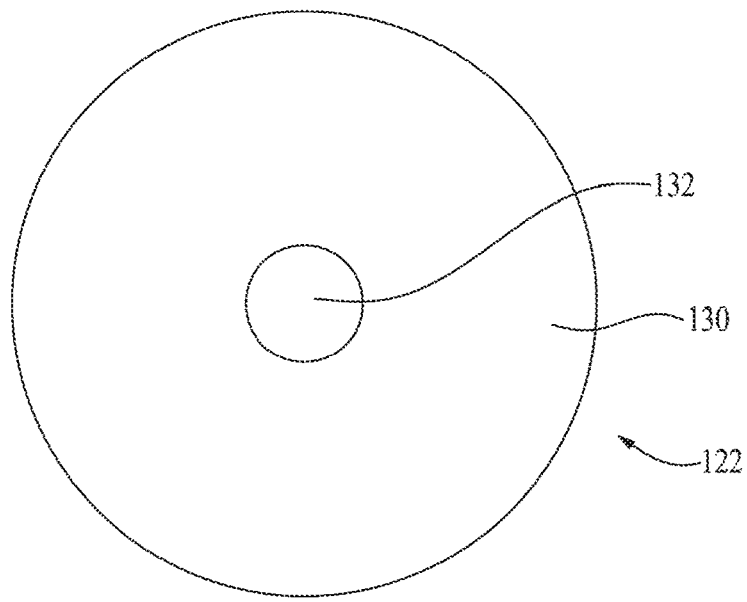
FIG. 14 is a back view of the movable fulcrum.

FIG. 14 is a back view of the movable fulcrum 122 and shows its back end 130 and its threaded through hole 132.

Figure 15:
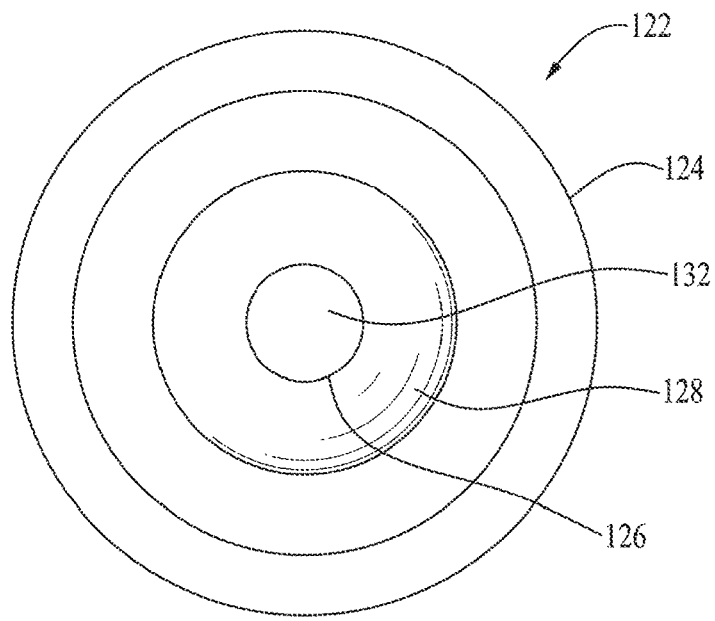
FIG. 15 is a front view of the movable fulcrum.

FIG. 15 is a front view of the movable fulcrum 122 and shows its knurled rim 124, its preferably domed structure 128 and the front region 126, and the threaded through hole 132.

Figure 16:
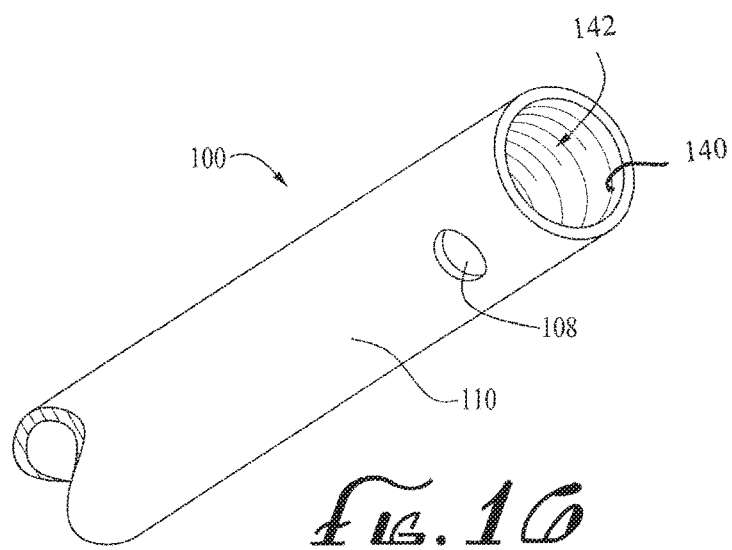
FIG. 16 is an isometric view showing internal threads formed in the inner sidewalls of the tubular structure.

FIG. 16 is an isometric view showing a portion of the proximal end 102 of the tubular structure 100, and shows internal threads 140 formed on the inside of the sidewalls 110 thereof. As noted above, the internal threads 140 could be right-hand or left-hand threads. The hollow interior 142 defined by the sidewall 110 is adapted to receive infill material, the dental post to be removed, and a dental tool, such as a Hedstrom file in the same manner as described with respect to FIG. 9B above. Also shown is one of the optional peripheral holes 108.

Figures 17A, 17B, 17C:
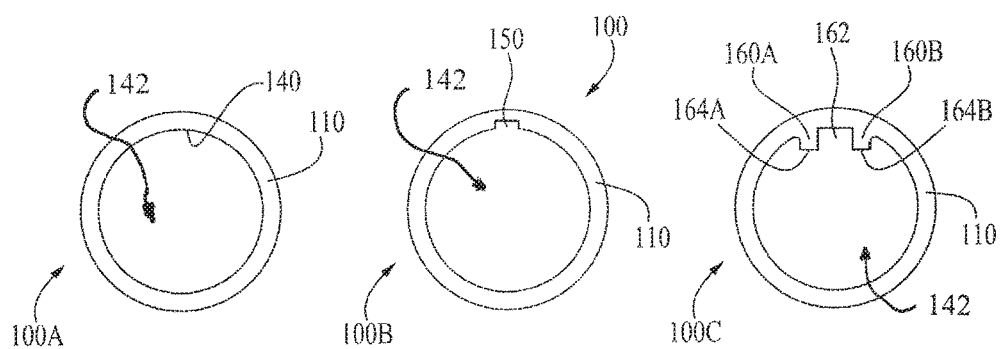
FIG. 17A is a cross-section view of the tubular structure of FIG. 16.
FIG. 17B is a cross-section view of the tubular structure having a longitudinal groove formed on the inside of the sidewall.
FIG. 17C is a cross-section view of the tubular structure having a pair of spaced apart longitudinal beads formed on the inside of the sidewall.

FIG. 17A is a cross-section view of the tubular structure 100A of FIG. 16, and shows its sidewalls 110 and internal threads 140 formed on the insides of the sidewalls. The hollow interior 142 defined by the sidewall 110 is shown.

FIG. 17B is a cross-section view of another tubular structure 100B having a longitudinal groove 150 formed on the inside of the sidewall 110. The longitudinal groove 150 is preferably formed along the entire length of the tubular structure 110 and is preferably a straight groove. While the groove 150 is shown as being generally rectangular in cross-section, it can have other profiles, such as being a V-shaped groove, a rounded bottom groove, or have other shapes. The groove 150 will be useful as it will tend to guide the Hedstrom file (not shown) when it is inserted into the hollow interior 142 defined by the sidewall 110.

FIG. 17C is a cross-section view of the tubular structure 100C having a pair of spaced apart longitudinal beads 160A and 160B formed on the inside of the sidewall 110. Between the two spaced apart longitudinal beads 160A and 160B an elongate region 162 is created that will act as a guide to direct movement of a dental tool, such as a Hedstrom file, when the tool is inserted into the hollow interior 142 defined by the sidewall 110. However, either of the outer side edges 164A and 164B of the longitudinal beads 160A and 160B, respectively, can function to help guide the Hedstrom file (not shown.) Although two longitudinal beads 160A and 160B are shown, it is possible to only have one longitudinal bead. Moreover, the shape of the bead can be altered as desired, and can be formed during the process of extruding the tubular structure, or can be affixed thereto.

Figure 18:
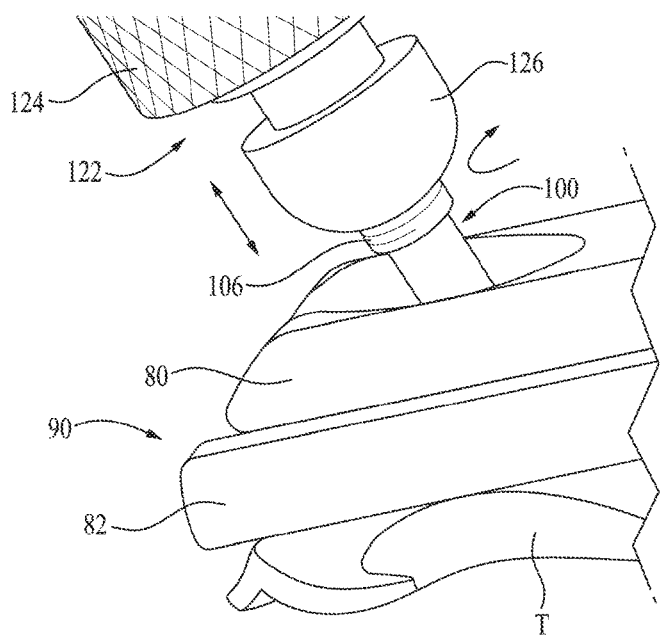
FIG. 18 is an isometric detail view showing the movable fulcrum on the tubular structure engaged with a pulling tool prior to the movable fulcrum being screwed down onto the pulling tool.

FIG. 18 is an isometric detail view showing the movable fulcrum 122 partially screwed onto the distal externally threaded region 104 of the tubular structure 100 (shown in FIG. 11A), with the tubular structure 100 engaged with a pulling tool prior to the movable fulcrum 122 being screwed down onto a dental post pulling tool engaging end 80 of post remover tool 90, which engaging end 80 rests on a tooth T.

Figure 19:
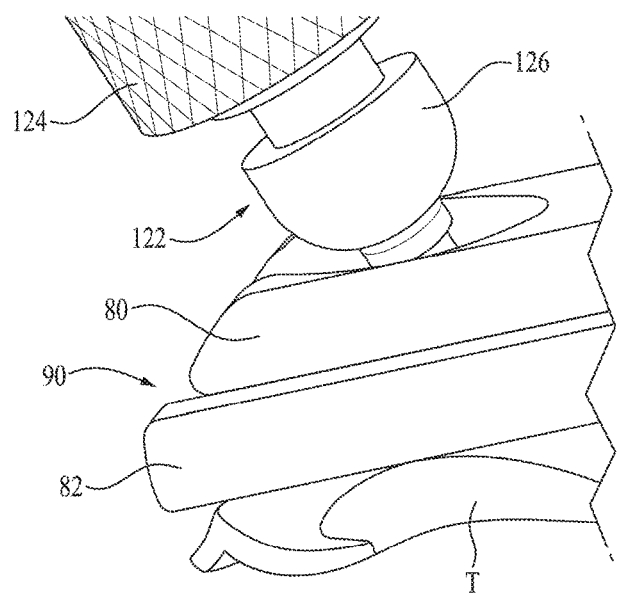
FIG. 19 is an isometric detail view showing the movable fulcrum on the tubular structure engaged with a pulling tool with the movable fulcrum screwed down nearly onto the pulling tool.

FIG. 19 is an isometric detail view showing the movable fulcrum 122 after being screwed down nearly all the way to where its front region 126 impinges on the dental post pulling tool engaging end 80 of post remover tool 90. When truly seated into the depression on the upper element of the Ruddle plier, there will be intimate contact between the global end of the nut and the depression.

Figure 20:
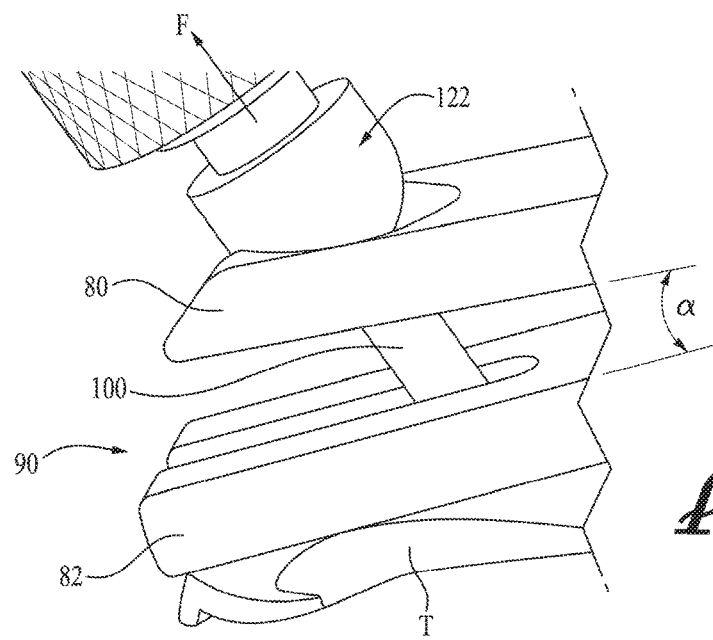
FIG. 20 is an isometric detail view showing the movable fulcrum on the tubular structure engaged with a pulling tool with the pulling tool partially activated to partially lift the tubular structure.
Figure 21:
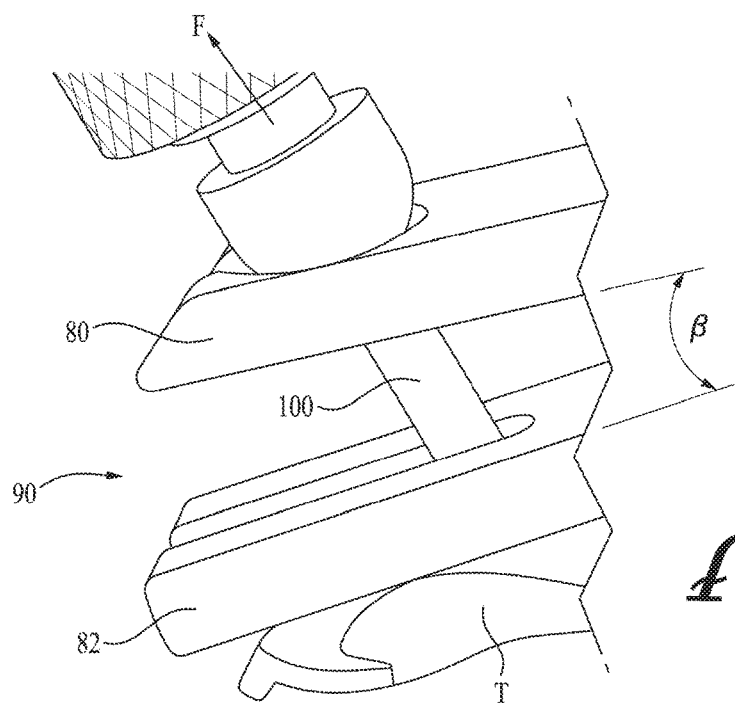
FIG. 21 is an isometric detail view showing the movable fulcrum on the tubular structure engaged with a pulling tool with the pulling tool further activated to further lift the tubular structure.

Referring also to FIG. 10, for example, in this state, when the dental post pulling tool 90 is operated to raise dental post removal tool engaging end 80 from the tooth contact end 82 thereof (as shown in FIGS. 20 and 21), a substantially upward force will also immediately act on the movable fulcrum 122 and its connected tubular structure 100 and the dental post engaged therewith (not shown). FIG. 20 shows the dental post pulling tool engaging end 80 and the tooth contact end 82 separated by an angle α, and FIG. 21 shows the dental post pulling tool engaging end 80 and the tooth contact end 82 separated further by an angle β, where angle α is less than angle β. At relatively small angles α and β, the pulling force F will almost exclusively consist of an upward force component, but as the angle becomes larger, there is more of a side force that would tend to pull perpendicular to the direction of the post. In order to keep the angles α and β relatively small, during the process of removing a dental post, the user can activate the pulling tool 90 by operating its knurl 86, the dental post removal tool engaging end 80 and the tooth contact end 82 will be moved apart from each other by a certain distance and angled apart from each other. To prevent the need to increase the angle, the user can turn the knurl 86 in an opposition direction to bring the dental post removal tool engaging end 80 and the tooth contact end 82 back into contact with each other, similarly as shown in FIG. 18, which will return the movable fulcrum 122 to a state where it is no longer impinging on the dental post pulling tool engaging end 80 of post remover tool 90. The user can next rotate the movable fulcrum 122 so that it is screwed down into contact with the dental post pulling tool engaging end 80 of the pulling tool 90, and then again activate the pulling tool 90 to further pull up the tubular structure 100 and its attached dental post (not shown). This process can be repeated until the post is freed from the tooth T. In practice, sometimes there is little or no movement of the dental post until it breaks loose. Thus, the dental post remover tool 90 may need to be untightened and reattached in different positions to aid in this process.

Although the movable fulcrum 122 is described as having a threaded through hole 132 which threadably engages with the male threads 106 of the externally threaded region 104 of the tubular structure 100, means other than threads can be used to change the position of the movable fulcrum 122 along the tubular structure 100. For example, the movable fulcrum can comprise a clamp with teeth that clamps onto complementary teeth formed on the tubular structure, wherein once the clamp is in place, it can only be moved further downwardly onto the tubular structure but will not move rearwardly. The teeth of the clamp can be spring loaded so that they engage with the tubular structure 100 and lock in place so that the clamp will not be movable rearwardly but can be pushed forwardly to contact a pulling tool.

Figure 22:
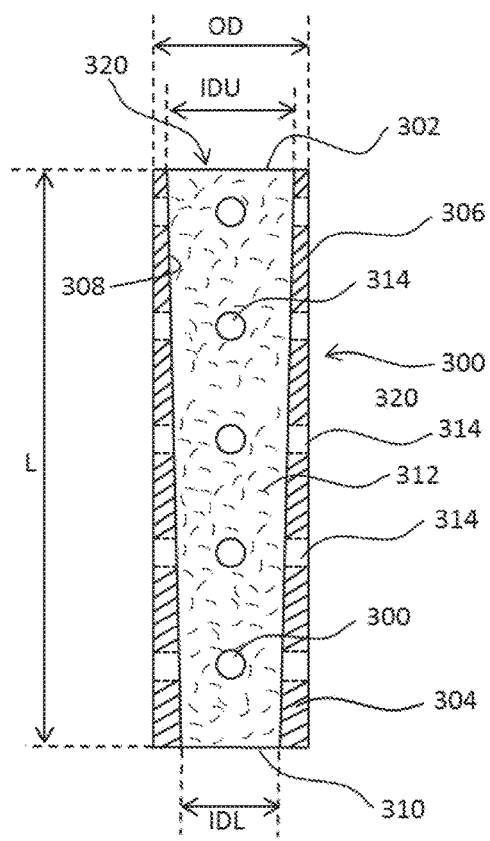
FIG. 22 is a cross-sectional view of another embodiment of a continuously internally tapered tubular structure of a dental post removal device of the invention.

Turning now to FIG. 22, there is shown a cross-sectional view of another embodiment of a continuously internally tapered tubular structure 300 of a dental post removal device of the invention. The tubular structure 300 does not show a fixing structure or a distal externally threaded region as with previously described embodiments, but will have one of these features located above an upper end 302 of the tubular structure 300. The tubular structure 300 has a perimeter wall 304 with an outer surface 306 and an inner surface 308. The tubular structure 300 has an outer diameter OD. The outer surfaces of the tubular structure 300 define generally parallel walls, but the inner surfaces bevel inwardly from the top 302 to the bottom opening 310, and the upper end 302 a larger inner diameter IDU and the lower end 310 as a smaller diameter IDL. Thus, a lumen 320 passing through the tubular structure 300 will be generally internally cone shaped, while the outside walls will remain parallel. Thus, the walls will be thicker near the lower end 310 and thinner near the upper end 302. This increased thickness at the open end provides greater pull through strength that will help prevent the tubular structure from possibly splitting. The inside surface of the walls are made to be adhesive enhanced 312 by roughening the surfaces, applying scratches, having a high adhesion coating, or even having inner threads formed on the inside walls. Since most hedstrom files are right hand threaded, it is preferable to include right-hand inner threads in the tubular structure so that they will engage with the right-hand flutes on the hedstrom file inserted into the lumen, and the hedstrom file engages with the notches created in the post, in the same manner as shown in the embodiment of FIG. 16. Alternately, it is also possible to include left handed inner threads in the tubular structure so that they will engage with the left-hand flutes on the hedstrom file inserted into the lumen.

Figure 23:
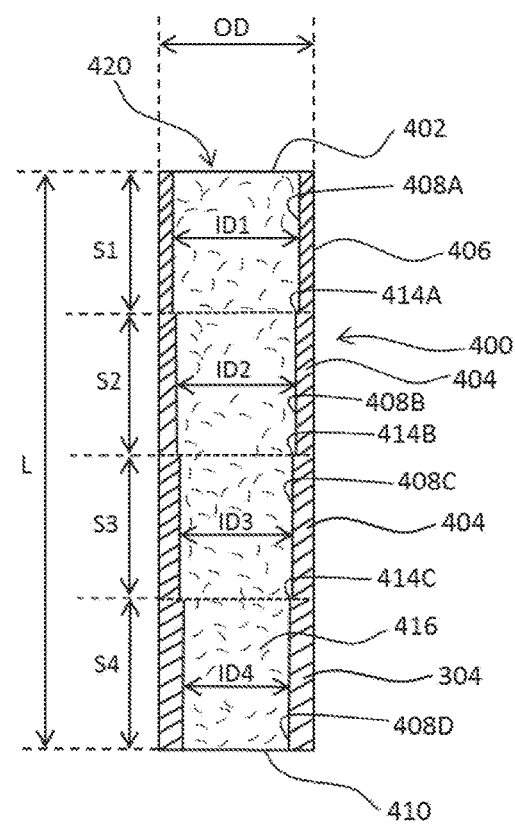
FIG. 23 is a cross-sectional view of yet another embodiment of a graduated parallel sided internally stepped tubular structure of a dental post removal device of the invention.

FIG. 23 is a cross-sectional view of yet another embodiment of a graduated parallel sided internally stepped tubular structure 400 of a dental post removal device of the invention. The tubular structure 400 does not show a fixing structure or a distal externally threaded region as with previously described embodiments, but will have one of these features located above an upper end 402 of the tubular structure 400. The tubular structure 400 has a perimeter wall 404 with an outer surface 406 and inner surfaces 408A-D located in stepped sections SA-SD. The tubular structure 400 has an outer diameter OD. In FIG. 23, four stepped sections S1, S2, S3, and S4 are shown, which have corresponding decreasing inner diameters from ID1, ID2, ID3, to ID4, respectively. The outer surface of the tubular structure 400 define generally parallel walls 406, and the series of stepped sections S1, S2, S3, and S4 also each have generally parallel walls, decreasing from a largest upper diameter ID1 to a smallest diameter ID4 in section SD near the bottom opening 410. In lieu of the internal walls being generally parallel, they can also be angled relative to each other so that the stepped sections are generally cone-shaped. In any case, a lumen 420 passing through the tubular structure 400 will be in the form of a stepped cone, while the outside walls will remain parallel. Thus, the walls will be thicker near the lower end 410 and thinner near the upper end 402. Although four stepped sections S1, S2, S3, and S4 are shown, a lesser or greater number of steps can be provided. In the transitions between the sections S1 and S2, S2 and S3, and S3 and S4, there are ledges 314A, 314B, and 314C. The inside surface 416 of the walls 404 are made to be adhesive enhanced by roughening the surfaces, applying scratches, having a high adhesion coating, or even having inner threads formed on the inside walls. This increased thickness at the open end provides greater pull through strength that will help prevent the tubular structure from possibly splitting.

Although embodiments of the present invention have been described in detail hereinabove in connection with certain exemplary embodiments, it should be understood that the invention is not limited to the disclosed exemplary embodiments, but, on the contrary is intended to cover various modifications and/or equivalent arrangements included within the spirit and scope of the present invention.

What is claimed is:

1. A method for removing a dental post from a tooth, comprising:
preparing a tooth with a dental post by removing cement, composite or other securing materials from around the dental post;
forming a plurality of indentations on the dental post to form a prepared dental post;
providing a dental post removal device comprising a hollow tubular structure having a sidewall and two opposite open ends, and a fulcrum positioned on the hollow tubular structure and adapted for pulling the hollow tubular structure, the hollow tubular structure being sized to fit over the prepared dental post;
filling the hollow tubular structure of the dental post removal device with dental composite resin, cement, and/or adhesive;
placing the material-filled tubular structure of the dental post removal device over the prepared dental post and inserting an elongate capture device through one open end of the material-filled tubular structure and engaging the elongate capture device between the prepared dental post and the wall of the tubular device and then allowing the material to polymerize, set or cure to secure together the tubular structure, the elongate capture device and dental post; and
applying an outward force on the fulcrum of the dental post removal device to remove the fulcrum and the attached elongate capture device and the prepared dental post from the tooth, wherein the fulcrum positioned on the hollow tubular structure of the dental post removal device is adjustably movable relative to the hollow tubular structure, wherein the movable fulcrum comprises a fulcrum body with a dome shaped front end that is adapted to seat precisely into a depression on a post pulling tool, and a female threaded through hole that passes therethrough, which fulcrum body is adapted to screw onto complementary male threads formed on a distal outer section of the tubular structure.

2. The method for removing a dental post from a tooth of claim 1, wherein a post pulling tool is interposed between a patient's tooth and movable fulcrum of the dental post removal device and the position of the adjustably movable fulcrum on the hollow tubular structure is adjusted so that the fulcrum is brought to a position wherein the fulcrum seats precisely into a depression on the post pulling tool thus engaging with the post pulling tool.

3. The method for removing a dental post from a tooth of claim 2, wherein the position of the movable fulcrum on the hollow tubular structure is repeatedly adjusted again after the post pulling tool is activated to ensure that a pulling force on the hollow tubular structure is generally coaxial with the attached dental post.

4. The method for removing a dental post from a tooth of claim 1, wherein the elongate capture device comprises a tapered fluted file.

5. The method for removing a dental post from a tooth of claim 1, wherein the hollow tubular structure comprises engaging features formed on the sidewall.

* * * * *